United States Patent [19]

Yamada

[11] Patent Number: 4,883,609
[45] Date of Patent: Nov. 28, 1989

[54] PYRIMIDINE DERIVATIVES
[75] Inventor: Shuhei Yamada, Nagano, Japan
[73] Assignee: Seiko Epson Corporation, Tokyo, Japan
[21] Appl. No.: 271,795
[22] Filed: Nov. 16, 1988
[30] Foreign Application Priority Data Nov. 17, 1987 [JP] Japan .................................. 62-289690

[51] Int. Cl.⁴ ........................ G02F 1/13; C09K 19/34; C07D 239/00; C07D 239/02
[52] U.S. Cl. ........................... 252/299.61; 350/350 R; 544/242; 544/335
[58] Field of Search ...................... 252/299.61, 299.66, 252/299.63; 350/350 R; 544/335, 242

[56] References Cited

U.S. PATENT DOCUMENTS

| 4,062,798 | 12/1977 | Boller et al. | 252/299.61 |
| 4,551,264 | 11/1985 | Eidensemink et al. | 252/299.63 |
| 4,640,795 | 2/1987 | Ogawa et al. | 252/299.61 |
| 4,664,840 | 5/1987 | Osman | 252/299.63 |
| 4,684,476 | 8/1987 | Kitano et al. | 252/299.61 |
| 4,776,975 | 10/1988 | Sawada et al. | 252/299.61 |

FOREIGN PATENT DOCUMENTS

| 3315295 | 10/1984 | Fed. Rep. of Germany | 252/299.61 |
| 3515373 | 11/1986 | Fed. Rep. of Germany | 252/299.61 |
| 60-54371 | 3/1985 | Japan | 252/299.61 |
| WO86/03769 | 7/1986 | World Int. Prop. O. | 252/299.61 |
| WO86/07055 | 12/1986 | World Int. Prop. O. | 252/299.61 |

Primary Examiner—Teddy S. Gron
Attorney, Agent, or Firm—Blum Kaplan

[57] ABSTRACT

Pyrimidine derivatives represented by the general formula:

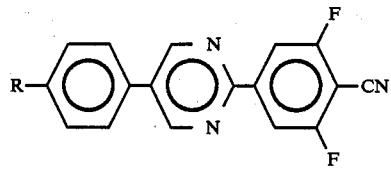

wherein R is a straight chain alkyl group having from 1 to 12 carbon atoms or an alkoxy group having from 1 to 12 carbon atoms. The pyrimidine derivatives are added to nematic liquid crystal compositions to reduce the threshold voltage of display devices by increasing the N→I transition temperature and the dielectric anisotropy.

9 Claims, 2 Drawing Sheets

PYRIMIDINE DERIVATIVES

BACKGROUND OF THE INVENTION

The invention relates generally to pyrimidine derivatives, and more particularly to pyrimidine derivatives which are suitable for use in nematic liquid crystal compositions to increase the N→I point and lower the threshold voltage.

Liquid crystal devices display information by making use of the electro-optical characteristics of liquid crystal materials. Specifically, these displays utilize the nematic liquid crystal phase. For example, the liquid crystal devices commonly include liquid crystal compounds of the twisted nematic, voltage controlled birefringence, guest-host and dynamic scattering types.

An improved twisted nematic compound, referred to as a super-twisted nematic compound has recently been developed. This super-twisted nematic compound has a twisted angle of from 180° to 250° compared to conventional nematic compounds which have a twist angle of 90°. Further, a super-twisted voltage controlled birefringence compound having a twisted angle of 270° in its stable condition has been proposed, but has not yet been developed for practical use.

Conventional liquid crystal display devices have many advantages. For example, they can be driven with low voltage and low power consumption, can be constructed in a small, flat shape and are not subject to fatigue because of the passive element structure even after use for long periods of time. These properties have allowed use of liquid crystal display devices in watches and time pieces, electronic calculators, automobile dashboards, audio mechanisms and the like. Recently an additional wide range of products, such as personal computers, word processors, pocket color televisions and other devices which had previously included CRT's.

The liquid crystal materials which are included in liquid crystal display devices must have certain properties. These are determined by the method of displaying and usage of the device. Twisted nematic liquid crystal compounds are widely used at present and their desireable properties include:

1. colorless and stable over a wide range of thermal, optical, electrical and chemical conditions;
2. useful over a wide range of temperatures;
3. high speed electro-optical response;
4. low driving voltage;
5. sharp rise time in voltage-light transmittance with a low temperature dependency; and
6. wide visual range.

The low driving voltage and use over a wide range of temperatures are particularly important properties. For the twisted nematic type the following relationship exists between the threshold voltage ($V_{th}$) and the dielectric anisotropy ($\Delta\epsilon$):

$$V_{th} = k\sqrt{\frac{K_{11} + \frac{1}{4}(K_{33} - 2K_{22})}{\Delta\epsilon}}$$

wherein $K_{11}$, $K_{12}$ and $K_{33}$ are elastic constants for the spray, twist, and bend of the compound, respectively and k is a proportional constant.

As is evident from this formula, in order to decrease the threshold voltage a large positive value of $\Delta\epsilon$ is required. However, conventional liquid crystal compounds which have a large $\epsilon$ such as 4-alkyl benzoic acid -4-cyanophenyl ester and 4-alkyl-4'-cyanobiphenyl have a low temperature at which the nematic phase undergoes a transition into the isotropic liquid phase (N→I point). This renders the nematic temperature range too narrow. Compounds having a higher N→I point and a large $\epsilon$, such as 4-alkyl-4'''-cyanoterphenyl, 4-(trans-4'-alkylcyclohexyl-4''-cyanobiphenyl and the like have a large elastic constant which increases the threshold voltage.

Accordingly, it is desirable to provide improved liquid crystal compositions for use in liquid crystal display devices which have high N→I points and a low threshold voltage.

SUMMARY OF THE INVENTION

Generally speaking, in accordance with the invention novel pyrimidine derivatives methods for forming these derivatives are provided. The new pyrimidine derivatives are represented by the general formula:

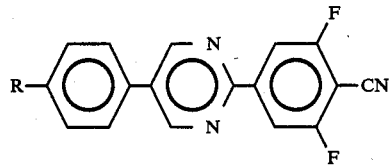

wherein R is a straight chain alkyl group having from 1 to 12 carbon atoms or an alkoxy group having from 1 to 12 carbon atoms. Pyrimidine derivatives prepared in accordance with the invention may be mixed with conventional liquid crystal compositions to increase the transition temperatures between the nematic phase and the isotropic liquid phase (N→I point) and provide large positive dielectric anisotropy ($\Delta\epsilon$).

Accordingly, it is an object of the invention to provide novel pyrimidine derivatives.

Another object of the invention is to provide novel pyrimidine derivatives which can be mixed with conventional liquid crystal compositions to increase transition temperatures and dielectric anisotropy.

A further object of the invention is to provide a method for preparing the novel pyrimidine derivatives.

Still another object of the invention is to provide improved liquid crystal display cells using liquid crystal compositions including the novel pyrimidine derivatives which will operate with a low driving voltage and over a wide range of temperatures.

Still other objects and advantages of the invention will in part be obvious and will in part be apparent from the specifications and drawings.

The invention accordingly comprises the several steps and the relation of one or more of such steps with respect to each of the others, and the liquid crystal device and the compounds possessing the features, properties, and the relation of constituents, which are exemplified in the following detailed disclosure, and the scope of the invention will be indicated in the claims.

BRIEF DESCRIPTION OF THE DRAWINGS

For a fuller understanding of the invention, references is had to the following description taken in connection with the accompanying drawings, in which.

DETAILED DESCRIPTION OF THE PREFERRED EMBODIMENTS

Figure 1:
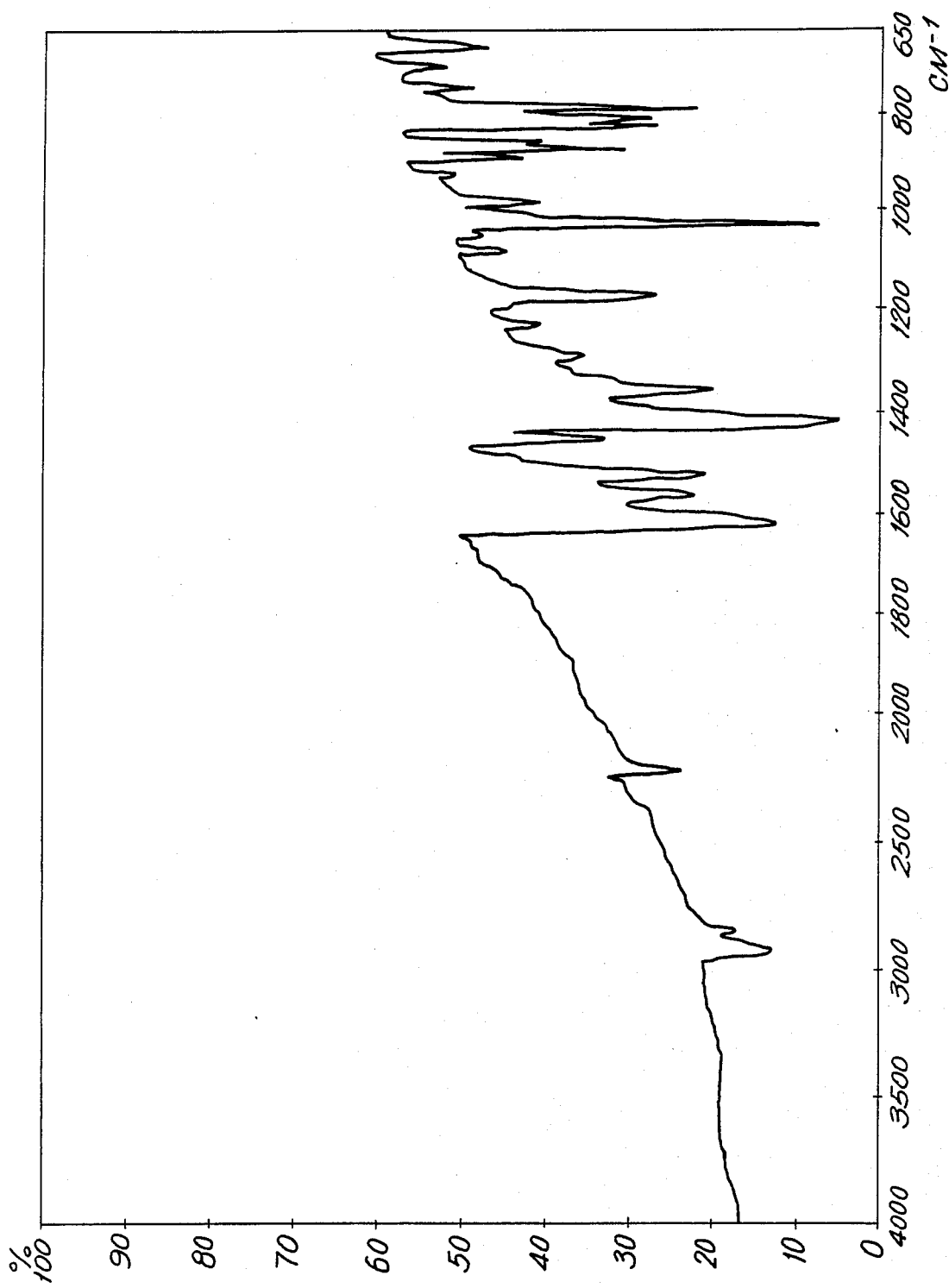
FIG. 1 is a graph showing the infrared spectra of 2-(3',5'-difluoro-4'-cyanophenyl)-5-(4''-butylphenyl), a pyrimidine derivative in accordance with the invention.

The novel pyrimidine derivatives prepared in accordance with the invention have the general formula:

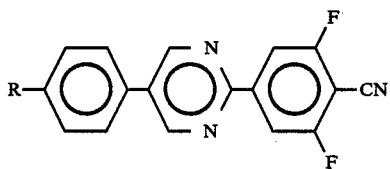

wherein R is a straight chain alkyl group having from 1 to 12 carbon atoms or alkoxy group having from 1 to 12 atoms. These pyrimidine derivatives may be included in a liquid crystal composition for use in a liquid crystal display cell to lower the threshold voltage by increasing the value of positive dielectric anisotropy (Δε) without adversely decreasing the transition temperature between the nematic phase and the isotropic liquid phase "N→I point". Preferably, between about 5 to 30 weight percent pyrimidine derivative is added to a liquid crystal composition having positive dielectric anisotropy. These features are desirable because they enable the liquid crystal device to have a low threshold voltage ($V_{th}$).

The following relationship exists for the threshold voltage and the dielectric anisotropy of a twisted nematic compound:

$$V_{th} = k \sqrt{\frac{K_{11} + \frac{1}{4}(K_{33} - 2K_{22})}{\Delta \epsilon}}$$

wherein $K_{11}$, $K_{22}$ and $K_{33}$ are elastic constants for the spray, twist and bend of the compound respectively and k is a proportional constant. Thus, in order to decrease the threshold voltage of the compound, a large positive Δε is required. Accordingly, the compounds of the invention are desirable in that they have a large positive Δε as well as a high N→I point.

Pyrimidine derivatives (1) prepared in accordance with the invention can be prepared by performing the following steps in which R is an alkyl group having from 1 to 12 carbon atoms or an alkoxy group having from 1 to 12 carbon atoms:

Step 1

An R-phenylacetylchloride (2) is reacted with phosphorous oxychloride in dimethyl formamide to yield a 1-dimethylamino-3-dimethylimino-2-(R-phenyl)-propene-(1)-perchlorate (3).

Step 2

A 2,6-difluoroaniline (4) is reacted with bromine in chloroform to yield 4-bromo-2,6-difluoroaniline (5).

Step 3

The 4-bromo-2,6-difluoroaniline (5) is reacted with copper (I) cyanide in N-methyl-2-pyrrolidone to yield 4-cyano-2,6-difluoroaniline (6).

Step 4

The 4-cyano-2,6-difluoroaniline (6) is reacted with sodium nitride and sulfuric acid in acetic acid to yield the diazonium salt and the resulting compound is reacted with copper (I) bromide in hydrobromic acid to yield 4-bromo-3,5-difluorobenzamidine hydrochloride (7).

Step 5

The 4-bromo-3,5-difluorobenzamidine hydrochloride (7) is reacted with dry hydrogen chloride gas in ethanol and benzene. The solvent is removed by distillation, and the resulting crystal is reacted with dry ammonia gas in ethanol to yield 4-bromo-3,5-difluorobenzamidine hydrochloride (8).

Step 6

The perchlorate (3) of Step 1 and the hydrochloride (8) of Step 5 are reacted with metallic sodium in methanol to yield 2-(3',5'-difluoro-4'-bromophenyl)-5-(4"-R-phenyl) pyrimidine (9).

Step 7

The pyrimidine (9) of Step 6 is reacted with copper (I) cyanide in N-methyl-2-pyrrolidone to yield 2-(3',5'-difluoro 4'-cyanophenyl)-5-(4"-R-phenyl) pyrimidine derivative (1).

The steps utilized to prepare the pyrimidine derivatives (1) are as follows:

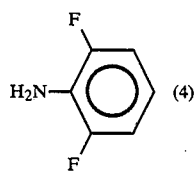

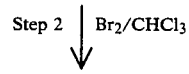

-continued

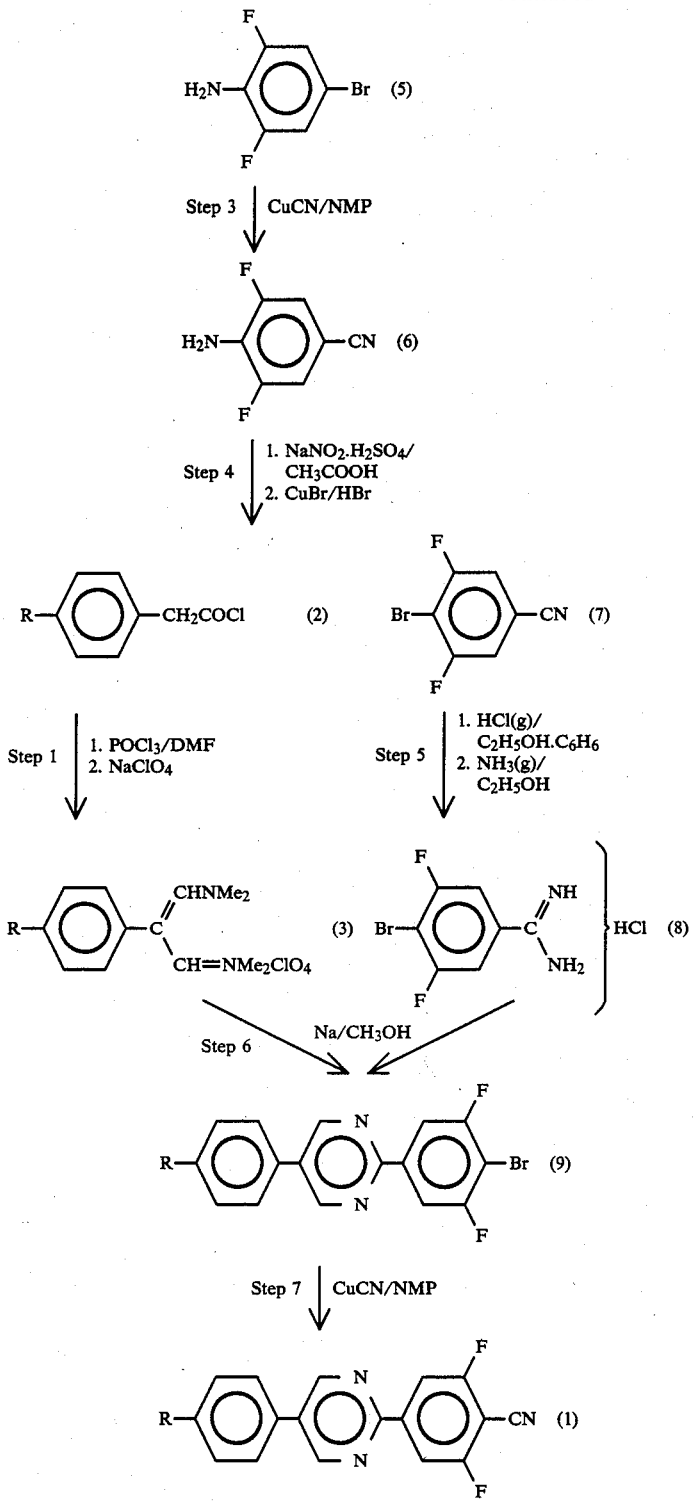

EXAMPLE 1

The pyrimidine derivative 2-(3',5'-difluoro-4'-cyanophenyl)-5-(4''-butylphenyl) pyrimidine, was prepared as follows. This example is presented for purposes of illustration only, and is not intended to be construed in a limiting sense.

Step 1

54 ml of phosphorous oxychloride was added dropwise to 230 ml of dimethylformamide and 42.1 g of 4-butylphenylacetylchloride was added dropwise. After stirring for three hours at a temperature of 70° C. and cooling the fluid, the dimethylformamide was removed by distillation. The residue was poured into ice water and the excess phosphorous oxychloride was dissolved. A solution containing 26 g of dissolved sodium perchlorate was added to the residue and the mixture was chilled to induce crystallization. The crystallized sample was filtered and recrystallization was repeated twice in ethanol to yield 58 g of 1-dimethylamino-3-dimethylimino-2-(4-butylphenyl)-propene-(1)-perchlorate.

Step 2

100 g of 2,6-difluoroaniline was dissolved in 180 ml of chloroform and 140 g of bromine was added dropwise. After one hour of reflux, the resulting solution was poured into a solution of 10% potassium hydroxide. The mixture was extracted with chloroform and the organic layer was washed with a solution of 10% potassium hydroxide in water. After the chloroform was removed by distillation, the residue was distilled under reduced pressure (bp 70° to 80° C. at 4 mmHg) and recrystallized with hexane to yield 127 g of 4-bromo-2,6-difluoroaniline.

Step 3

21 g of 4-bromo-2,6-difluoroaniline, 11 g of copper (I) cyanide, and 70 ml of N-methyl-2-pyrrolidone were placed in a flask for three hours to form a reaction mixture. The reaction mixture was poured into a solution of 41 g of iron (III) chloride mixed with 13 ml of concentrated hydrochloric acid and 50 ml of water. The mixture was extracted with chloroform and washed with water and 10% potassium hydroxide and the chloroform was removed by distillation. The residue was distilled under reduced pressure (bp 90° to 110° C. at 4 mmHg) and recrystallized with a mixture of hexane and chloroform to yield 8.9 g of 4-cyano-2,6-difluoroaniline.

Step 4

4 g of sodium nitride was added to 30 ml of concentrated sulfuric acid and chilled to a temperature of 10° C. and 38 ml of acetic acid was added thereto. 8.9 ml of 4-cyano-2,6-difluoroaniline was added gradually to maintain the solution at a temperature of 20° to 25° C. The reaction mixture was added dropwise to a solution a 10 g of copper (I) bromide dissolved in 30 ml of concentrated hydrobromic acid. After the dropwise addition was completed, the reaction mixture was stirred for one and one half hours at room temperature. Water was added to the reaction mixture, the reaction mixture was extracted with chloroform and washed with water. The organic layer was removed by distillation, and the residue was recrystallized with a mixture of methanol and acetone to yield 6.6 g of 2-bromo-5-cyano-1,3-difluorobenzene.

Step 5

2 g of 2-bromo-5-cyano-1,3-difluorobenzene was dissolved in a solution of 4 ml of ethanol and 15 ml benzene and chilled to a temperature below 0° C. 16% ammonia absorption ethanol was added to the chilled solution which was then stirred for one hour. After the reaction was completed, the solvent of the solution was distilled off and the crystal residue was washed with ether to yield 2.1 g of 4-bromo-3,5-difluorobenzamidine hydrochloride.

Step 6

2.1 g of 4-bromo-3,5-difluorobenzamidine hydrochloride and 2.7 g of 1-dimethylamino-3-dimethylimino-2-(4-butylphenyl)-propene-(1)-perchlorate from Step 1 were dissolved in 28 ml of methanol and a sodium methylate solution formed of 0.4 g of metallic sodium in 14 ml of methanol was added dropwise. The mixture was stirred overnight at room temperature and refluxed for one hour. This reaction solution was chilled, and water was added. Deposited crystals were filtered out. The solution was recrystallized in a mixture of acetone and methanol to yield 2.1 g of 2-(3',5'-difluoro-4'-(bromophenyl)-5-(4''-butylphenyl) pyrimidine.

Step 7

2.1 g of 2-(3', 5'-difluoro-4'-bromophenyl)-5-(4''-butylphenyl) pyrimidine, 0.8 g of copper (I) cyanide, and 6 ml of N-methyl-2-pyrrolidone were mixed in flask and the mixture was refluxed for one and one half hours. The resulting solution was combined with a mixture of 2.7 g of iron (III) chloride, 0.6 ml of concentrated hydrochloric acid, and 2.7 ml of water. This mixture was extracted with chloroform, and washed with water and 10% of potassium hydroxide. The chloroform was removed by distillation and the residue was recrystallized in a mixture of acetone and methanol to yield 0.5 g of 2-(3',5'-difluoro-4'-cyanophenyl)-5-(4''-butylphenyl) pyrimidine.

The resulting pyrimidine derivative exhibited nematic liquid crystal properties, and had a melting point of 101° C. and an N→I point of 144° C. This pyrimidine derivative has the infra-red spectra shown in FIG. 1.

EXAMPLE 2

The following pyrimidine derivatives prepared in accordance with the invention can be prepared in a similar manner and have the properties indicated. C→N symbolizes the transition temperature from the crystal phase to the nematic phase. N→I symbolizes the transition temperature from the nematic phase to the isotropic liquid phase.

2-(3', 5'-difluoro-4'-cyanophenyl)-5-(4''-methylphenyl) pyrimidine
2-(3', 5'-difluoro-4'-cyanophenyl)-5-(4''-ethylphenyl) pyrimidine
    C→N 171° C.,    N→I 163° C.
2-(3', 5'-difluoro-4'-cyanophenyl)-5-(4''-propylphenyl) pyrimidine
    C→N 136° C.,    N→I 155.5° C.
2-(3', 5'-difluoro-4'-cyanophenyl)-5-(4''-pentylphenyl) pyrimidine
    C→N 114.5° C.,    N→I 145.5° C.
2-(3', 5'-difluoro-4'-cyanophenyl)-5-(4''-hexylphenyl) pyrimidine
2-(3', 5'-difluoro-4'-cyanophenyl)-5-(4''-hexylphenyl) pyrimidine
    C→N 108° C.,    N→I 142° C.
2-(3', 5'-difluoro-4'-cyanophenyl)-5-(4''-octylphenyl) pyrimidine
2-(3', 5'-difluoro-4'-cyanophenyl)-5-(4''-octylphenyl) pyrimidine
2-(3', 5'-difluoro-4'-cyanophenyl)-5-(4''-decylphenyl) pyrimidine
2-(3', 5'-difluoro-4'-cyanophenyl)-5-(4''-undecylphenyl) pyrimidine
2-(3', 5'-difluoro-4'-cyanophenyl)-5-(4''-dodecylphenyl) pyrimidine
    C→N 121° C.,    N→I 140° C.
2-(3', 5'-difluoro-4'-cyanophenyl)-5-(4''-methoxyphenyl) pyrimidine
2-(3', 5'-difluoro-4'-cyanophenyl)-5-(4''-ethoxyphenyl) pyrimidine
    C→N 170° C.,    N→I 165° C.
2-(3', 5'-difluoro-4'-cyanophenyl)-5-(4''-propyloxyphenyl) pyrimidine
    C→N 135° C.,    N→I 193° C.
2-(3', 5'-difluoro-4'-cyanophenyl)-5-(4''-butyloxyphenyl) pyrimidine
2-(3', 5'-difluoro-4'-cyanopheny)-5-(4''-pentyloxyphenyl) pyrimidine
    C→N 106.5° C.,    N→I 179° C.
2-(3', 5'-difluoro-4'-cyanophenyl)-5-(4''-hexyloxyphenyl) pyrimidine
    C→N 132.5° C.,    N→I 175.5° C.
2-(3', 5'-difluoro-4'-cyanophenyl)-5-(4''-heptyloxyphenyl) pyrimidine
2-(3', 5'-difluoro-4'-cyanophenyl)-5-(4''-octyloxyphenyl) pyrimidine
2-(3', 5'-difluoro-4'-cyanophenyl)-5-(4''-nonyloxyphenyl)

-continued pyrimidine
       C→N 124° C.,           N→I 168° C.
2-(3', 5'-difluoro-4'-cyanophenyl)-5-(4"-decyloxyphenyl)
pyrimidine
2-(3', 5'-difluoro-4'-cyanophenyl)-5-(4"-undecyloxyphenyl)
pyrimidine
2-(3',5'-difluoro-4'-cyanophenyl)-5-(4"-dodecyloxyphenyl)
pyrimidine
       C→N 143° C.,           N→I 165° C.

EXAMPLE 3

The ability of the pyrimidine derivatives of compound (1) in which R is a butyl group to lower the threshold voltage of a liquid crystal device without lowering the N→I point was evaluated as follows: 2-(3', 5,-difluoro-4'-cyanophenyl)-5-(4"-butyphenyl) pyrimidine from Example 1 was compared with 4-pentyl-4"-terphenyl, a compound which is commonly used to improve the N→I point in liquid crystal cells. Both compounds were combined with ZLI-1565 (made by Merck Co., Ltd.), a base mixed liquid crystal composition having an N→I point of 89.3° C., in the following proportions:

| Composition A | |
|---|---|
| ZLI-1565 | 90% part by weight |
| 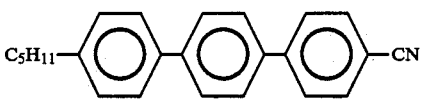 | 10% part by weight |

| Composition B | |
|---|---|
| ZLI-1565 | 90% part by weight |
| 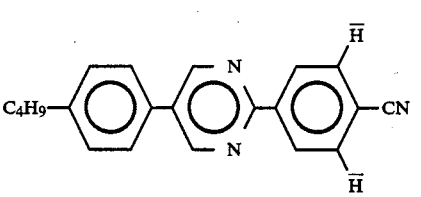 | 10% part by weight |

Figure 2:
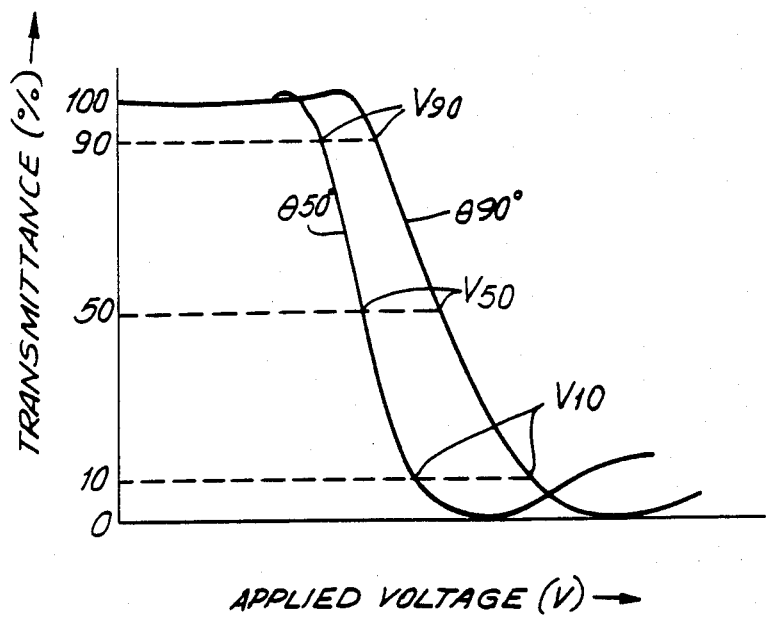
FIG. 2 is a graph showing the voltage transmittance characteristics of a twisted nematic liquid crystal cell.
Figure 3:
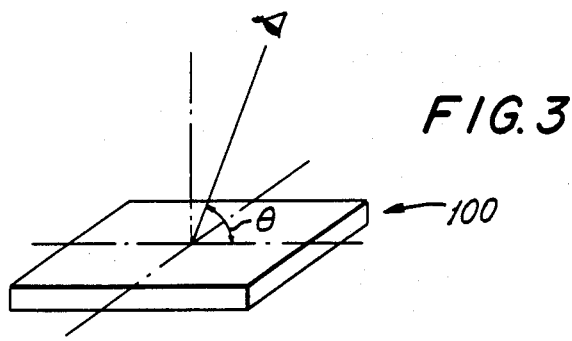
FIG. 3 is a schematic diagram illustrating the direction for measuring the angle θ of view of the cell of FIG. 2.
Figure 4:
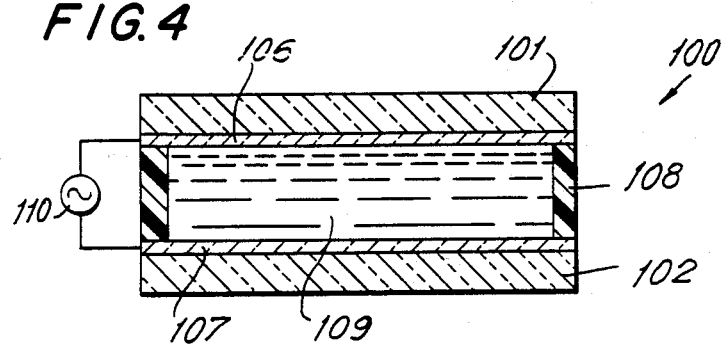
FIG. 4 is a cross-sectional view of a liquid crystal cell.

Comparison Composition A and Composition B including pyrimidine derivative (1) from Example 1 were each prepared and used to fill 7 μm thick TN cells shown as 100 in FIG. 4. Cell 100, shown in cross-section in FIG. 4 includes a pair of opposed substrates 101 and 102, at least one of which is transparent. The interior surfaces of substrates 101 and 102 have an electrode 106 and an electrode 107 disposed thereon coupled to a power supply 110. A seal 108 is provided to enclose a liquid crystal composition 109 in the space between substrates 101 and 102. Afterwards, the voltage-transmittance properties under alternating static driving at a temperature of 25° C. were measured, as shown in FIG. 2. The results are shown in Table 2. The direction for measuring angle θ is shown in FIG. 3. A curve θ50° of FIG. 2 shows the voltage transmittance property for θ=50° and θ90° is the curve for θ=90°. $V_{10}$, $V_{50}$ and $V_{90}$ show the voltages for when transmittance equals 10%, 50% and 90% respectively.

TABLE 2

| Composition | N→I point | $V_{10}$ | α | β |
|---|---|---|---|---|
| A | 105.5 | 2.344 | 1.289 | 1.412 |
| B | 92.9 | 1.794 | 1.277 | 1.375 |

In Table 2, $V_{10}$ is the voltage value during 10% transmittance, and V is a measured value from the measuring direction of the TN cell for θ=90° C. α and β are factors showing the view angle properties and threshold properties, respectively, as defined below.

$$\alpha = \theta 90° \ V_{50}/\theta 50° \ V_{50}$$

$$\beta = \theta 90° \ V_{10}/\theta 90° \ V_{90}$$

As discussed above, by mixing a pyrimidine derivative having the formula (1) in accordance with the invention with a general liquid crystal composition, the N→I point increases, the value of threshold voltage is greatly reduced, and the electrooptical properties (α value and β value) are improved. Accordingly pyrimidine derivatives prepared in accordance with the invention are useful as the basic components of a liquid crystal composition which includes the super twisted nematic type display that are currently being used in liquid crystal display devices. These pyrimidine derivatives have a high molecular weight to maintain a high N→I point and have high electro-negativity due to the presence of the cyano and fluoro groups which yields a cell which can be driven by a low driving voltage.

It will thus be seen that the objects set forth above, among those made apparent from the preceding description, are efficiently attained and, since certain changes may be made in carrying out the above method and in the composition set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

Particularly it is to be understood that in said claims, ingredients or compounds recited in the singular are intended to include compatible mixtures of such ingredients wherever the sense permits.

What is claimed:

1. A pyrimidine derivative having general formula:

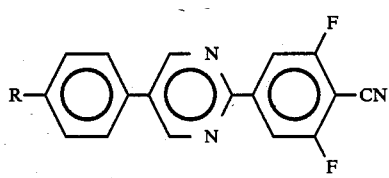

wherein, R is one of a straight chain alkyl group having from 1 to 12 carbon atoms and an alkoxy group having from 1 to 12 carbon atoms.

2. The pyrimidine derivative of claim 1, wherein R includes from 3 to 6 carbon atoms.

3. The pyrimidine derivative of claim 1, wherein R is butyl and the pyrimidine derivative is 2-(3',5'-difluoro-4'-cyanophenyl)-5-(4''-butylphenyl) pyrimidine.

4. A liquid crystal composition comprising at least one nematic liquid crystal compound and an effective amount of pyrimidine derivative having the general formula:

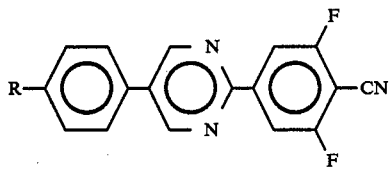

in which R is one of a straight chain alkyl group having from 1 to 12 carbon atoms and an alkoxy group having from 1 to 12 carbon atoms for reducing the threshold voltage without adversely increasing the N→I transition point.

5. The liquid crystal composition of claim 4, wherein the pyrimidine derivative is present in an amount between 5 and 30 percent by weight of the total liquid crystal composition.

6. A method of forming a pyrimidine derivative having the formula:

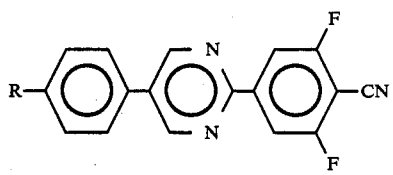

wherein R is one of an alkyl group having from 1 to 12 carbon atoms and an alkoxy group having from 1 to 12 carbon atoms, comprising:
reacting an R-phenylacetylchloride with phosphorous oxychloride in dimethyl formamide to yield a 1-dimethylamino-3-dimethylimino-2-(R-phenyl)-propene-(1)-perchlorate;
reacting 2,6-difluoroaniline with bromine in chloroform to yield 4-bromo-2,6-difluoroaniline;
reacting 4-bromo-2,6-difluoroaniline with copper (I) cyanide and N-methyl-2-pyrrolidone to yield 4-cyano-2,6-difluoroaniline;
reacting 4-cyano-2,6-difluoroaniline with sodium nitride and sulfuric acid in acetic acid to yield the diazonium salt which is reacted with copper (I) bromide in hydrobromic acid to yield 4-bromo-3,5-difluorobenzamidine hydrochloride;
reacting 4-bromo-3,5-difluorobenzamidine hydrochloride with hydrogen chloride gas in ethanol and benzene; removing all solvents by distillation and reacting the resulting crystal with dry ammonia gas in ethanol to yield 4-bromo-3,5-difluorobenzamidine hydrochloride;
reacting 1-dimethylamino-3-dimethylammonio-2-(R-phenyl)-propene-(1)-perchlorate with 4-bromo-3,5-difluorobenzamidine hydrochloride with metallic sodium in methanol to yield 2-(3',5'-difluoro-4'-bromophenyl)-5-(4''R-phenyl) pyrimidine; and
reacting 2-(3',5'-difluoro-4'-(bromophenyl)-5-(4''R-phenyl) pyrimidine with copper (I) cyanide in N-methyl-2-pyrrolidone to yield 2-(3',5'-difluoro-4'cyanophenyl)-5-(4''-R-phenyl) pyrimidine.

7. The method of claim 6, wherein R is n-butyl.

8. A liquid crystal display cell including a nematic liquid crystal composition and an effective amount of pyrimidine derivative having the general formula:

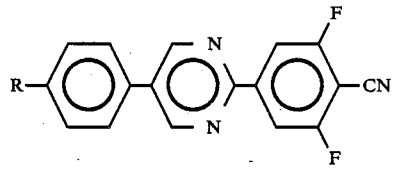

wherein, R is one of a straight chain alkyl group having from 1 to 12 carbon atoms and an alkoxy group having from 1 to 12 carbon atoms for reducing the threshold voltage of the composition without adversely increasing the N→I transition temperature.

9. The liquid crystal cell of claim 8, wherein R is n-butyl.

* * * * *